(12) United States Patent
Hahn et al.

(10) Patent No.: US 6,325,979 B1
(45) Date of Patent: Dec. 4, 2001

(54) DEVICE FOR GAS-SENSORING ELECTRODES

(75) Inventors: Dieter Hahn, Gerlingen; Gottfried Flik, Leonberg; Bernd Schumann, Rutesheim, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/284,661
(22) PCT Filed: Oct. 15, 1997
(86) PCT No.: PCT/DE97/02356
  § 371 Date: Jun. 7, 1999
  § 102(e) Date: Jun. 7, 1999
(87) PCT Pub. No.: WO98/16819
  PCT Pub. Date: Apr. 23, 1998

(30) Foreign Application Priority Data

Oct. 15, 1996 (DE) .............................................. 196 42 453

(51) Int. Cl.[7] .............................. H01C 7/00; G01N 27/26
(52) U.S. Cl. ............................. 422/88; 204/432; 204/431; 204/424; 204/426; 338/34; 73/23.2; 422/98; 422/83

(58) Field of Search .................................. 422/88, 83, 98; 338/34, 35; 73/23.2; 204/432, 430, 431, 415

(56) References Cited

U.S. PATENT DOCUMENTS

| | | |
|---|---|---|
| 5,086,286 | 2/1992 | Yasukawa et al. |
| 5,522,980 * | 6/1996 | Hobbs et al. .......................... 204/432 |
| 5,538,620 * | 7/1996 | Nikolskaja ............................ 205/782 |
| 5,560,810 * | 10/1996 | Capetanopolous et al. .......... 204/408 |
| 5,698,771 * | 12/1997 | Shields et al. ....................... 73/31.05 |
| 5,841,021 * | 11/1998 | De Castro et al. .................... 73/23.2 |

FOREIGN PATENT DOCUMENTS

| | | |
|---|---|---|
| 0 488 352 A | 6/1992 | (EP) . |
| 0 529 668 A | 3/1993 | (EP) . |

* cited by examiner

Primary Examiner—Jill Warden
Assistant Examiner—Brian Sines
(74) Attorney, Agent, or Firm—Kenyon & Kenyon

(57) ABSTRACT

A sensing element, in particular for an electrochemical sensor for determining gas concentrations, having at least one three-dimensional electrode arrangement, applied on a support plate and forming trenches of a depth for measuring changes in capacitance and/or conductivity in a gas-sensitive layer arranged to a height in the trenches, the height of the gas-sensitive layer being less than the depth of the trenches.

9 Claims, 6 Drawing Sheets

DEVICE FOR GAS-SENSING ELECTRODES

FIELD OF THE INVENTION

The present invention is based on a sensing element, in particular for an electrochemical measurement sensor for determining gas concentrations.

BACKGROUND INFORMATION

The use of planar electrode arrangements for chemical sensors is known. The gas concentrations are ascertained by determining changes in capacitance and/or conductivity in a gas-sensitive material. Also known is the three-dimensional configuration of electrode arrangements, which further increases the sensitivity of chemical sensors (Lin et al., Sensors and Actuators 5 (1991), 223 to 226). According to Lin et al., the manufacture of three-dimensional electrode arrangements is accomplished by first sputtering a metallic film onto a silicon substrate and then patterning a photoresist applied upon patterning of the photoresist, the resulting trenches are filled by electroplating, yielding a three-dimensional electrode structure as an inverse resist structure. After removal of the photoresist, the trenches, i.e, the electrode interstices, are filled with a gas-sensitive substance.

SUMMARY

The sensing element has, the advantage that the three-dimensional structure of the electrode arrangement can be used as a retaining structure for catalytically active layers and/or protective layers, and locally as a wall catalyst. Because the gas-sensitive material introduced into the trenches does not fill them up completely, it is on the one hand possible to cover over the gas-sensitive material with catalyst layers and/or protective layers, and/or on the other hand to use regions of the three-dimensional electrode arrangement which are not covered by gas-sensitive material or other layers as a wall catalyst. In the embodiments according to the present invention in which the gas-sensitive material is covered over with protective layers and/or catalytically active layers, the three-dimensional structure of the electrode arrangement acts as a retaining structure for those layers, and guarantees a stable configuration for the sensing element. In the embodiments according to the present invention in which the inner walls, i.e. the walls forming the trenches, of the three-dimensional electrode arrangement are not completely covered by the aforesaid layers which cover the gas-sensitive material, the inner walls can be used as a wall catalyst. The use of catalytic layers covering the gas-sensitive material and/or the use of the inner walls of the three-dimensional electrode arrangement as a wall catalyst is advantageous, and after "particular" in particular if the gas-sensitive material does not exhibit complete selectivity for the gas to be measured. In such a case it is particularly desirable to subject the gas mixture being investigated to catalysis, the gas to be detected being catalytically converted in such a way that it is detected by the gas-sensitive layer and determined as selectively as possible. According to the present invention, improved selectivity of the gas measurement in the gas-sensitive material can be achieved by using a catalytically active layer and/or by wall catalysis. The use of additional catalytically active layers can be dispensed with, since the conversion into the specific gas to be detected is accomplished by inner-wall catalysis.

The present invention also provides that the height h of the gas-sensitive layer introduced into the trenches, or the depth T of the trenches, can vary, although in every region of the trench the height h is to be substantially less than depth T of the trenches.

BRIEF DESCRIPTION OF THE DRAWINGS

FIG. 1$a$ shows a step of applying an electroplating starter layer.

FIG. 1$b$ shows a step of applying a photoresist layer.

FIG. 1$c$ shows a step of transferring a metallic three-dimensional electrode arrangement into the photoresist layer.

FIG. 1$d$ shows a step of depositing metal into resist trenches.

FIG. 1$e$ shows a step of dissolving the photoresist layer.

FIG. 1$f$ shows a step of producing a heating electrode.

FIG. 1$g$ shows a step of removing electroplating starter layers.

FIG. 1$h$ shows a step of placing a paste into interstices between electrodes.

DETAILED DESCRIPTION

Figure 1A:
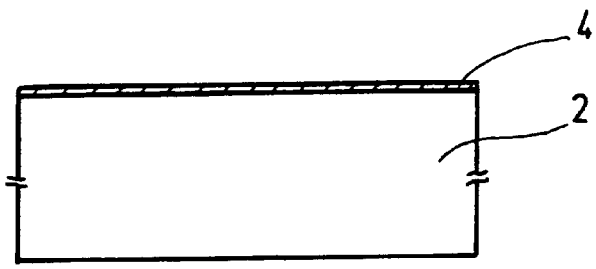
FIGS. 1$a$–1$h$ show in schematic sequence, a process steps for manufacturing a sensing element which includes three-dimensional miniaturized electrode arrangements according to one embodiment of the present invention, the sensing element being depicted in longitudinal sections.
Figure 1B:
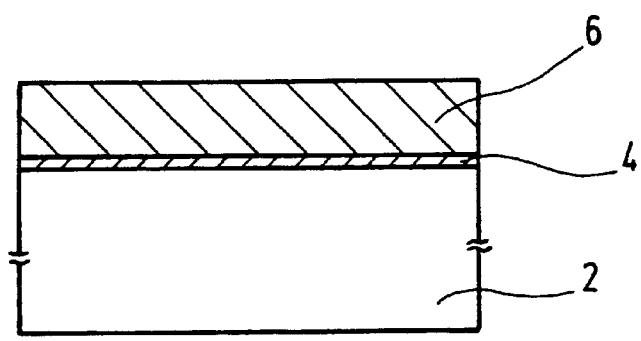
Figure 1C:
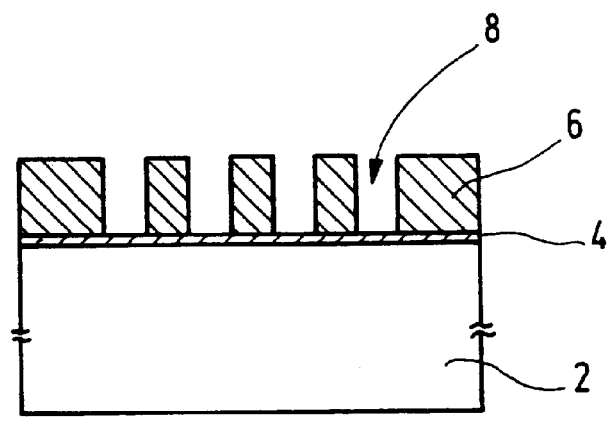
Figure 1D:
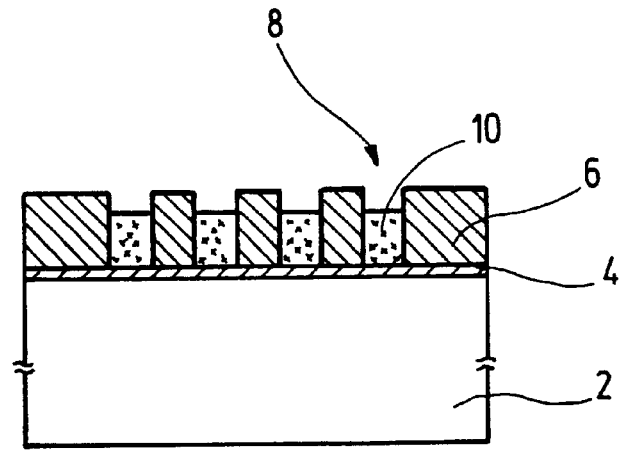
Figure 1E:
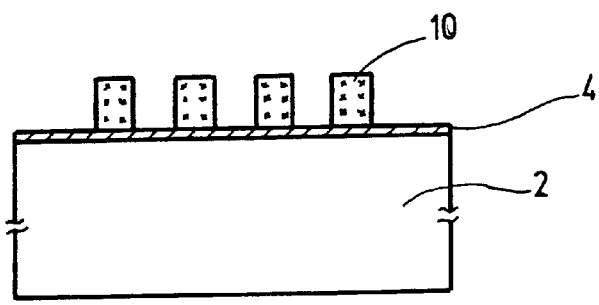
Figure 1F:
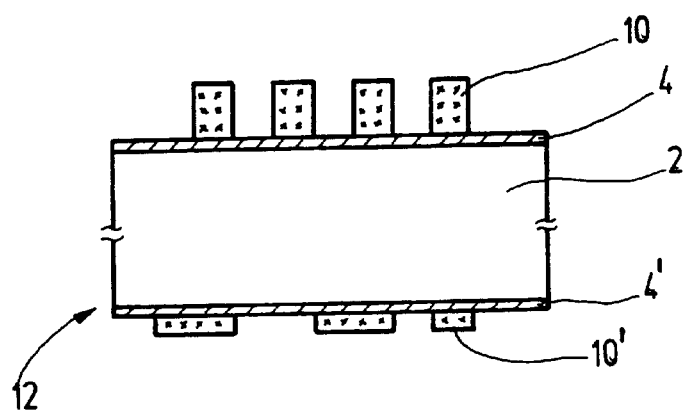
Figure 1G:
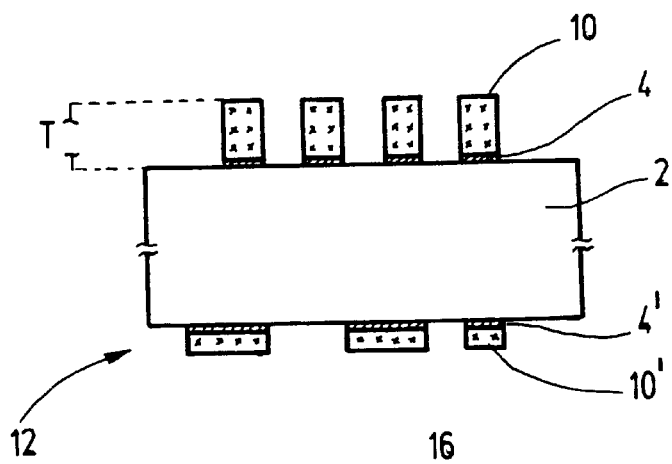
Figure 1H:
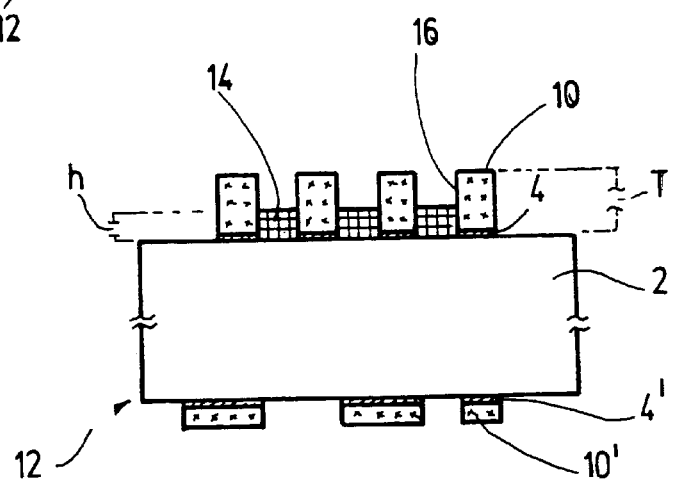

FIGS. 1$a$–1$h$ shows, in schematic sequence, the process steps a) through h) for manufacturing three-dimensional miniaturized electrode arrangements. In step a), (FIG. 1$a$), after a cleaning step, an electroplating starter layer 4 is applied by sputtering onto a flat support plate 2. Especially if the sensor to be manufactured is to be used in highly corrosive media, for example in exhaust gas diagnosis, support plate 2 can be made $Al_2O_3$, onto which platinum is applied as the electroplating starter layer. If the requirements in terms of corrosion resistance are less stringent, other substrates such as silicon or glass can be used, and metals such as gold, silver, copper, chromium, and others can be used to manufacture the electroplating starter layer. If the sensors are to be integrated with an electronic analysis system, the use of silicon substrates is particularly advantageous.

In step b), (FIG. 1$b$), a photoresist layer 6, for example a photoresist, polyimide, or solid resist, is then applied onto the entire surface of support plate 2, by spin-coating (for liquid resists) or by rolling (for solid resists). The film thickness of photoresist layer 6 is adjusted by way of the rotation speed for liquid resists, and by way of the number of rolled-on resist layers, for solid resists. According to an example embodiment film thicknesses between 10 μm and 100 μm may be used.

In step c), (FIG. 1c) the metallic three-dimensional electrode arrangement that is to be manufactured is transferred inversely into photoresist layer 6 by way of a photolithographic mask. In a deep UV lithographic method, the resist is illuminated directly through a mask. Another possibility is to deposit onto the photoresist an oxide, a nitride, or a metal which is photolithographically patterned as a mask for a dry etching process of photoresist layer 6. Smaller pattern widths can be manufactured with the dry etching process than with the deep UV lithographic method. Both alternatives result in the formation of resist trenches 8 in photoresist layer 6.

In step d), (FIG. 1d) metal is deposited into resist trenches 8; resist trenches 8 can be filled up to their upper edge. By varying the thickness of metal layer 10, it is possible to adjust the sensor sensitivity in controlled fashion. Selection of the material to be deposited depends on the corrosion resistance required for the sensor: platinum, gold, and silver are thus possible for stringent requirements, and metals such as copper, nickel, or the like for lesser requirements.

In step e), (FIG. 1e) photoresist layer 6 is dissolved out of the applied metal structure 10, resulting in free-standing three-dimensional electrode structures. Alkaline solutions such as a potassium hydroxide solution, or organic solvents such as acetone, can be used depending on the photoresist that is utilized.

In step f), (FIG. 1f) according to the example embodiment of the present invention a heating electrode can be produced on rear side 12 of support plate 2 so that the sensor can be kept at a constant temperature. The geometry of heating electrode 10' is defined by a mask pattern, and patterning is performed as described in steps a) through e).

In step g), (FIG. g) electroplating starter layers 4 and 4' are removed in order to interrupt the conductive connections between electrodes 10 of the sensor and also of heater 10'. The electroplating starter layers are removed by etching them away, for example by wet-chemical etching, anionic etching, or a dry etching process.

Figure 5:
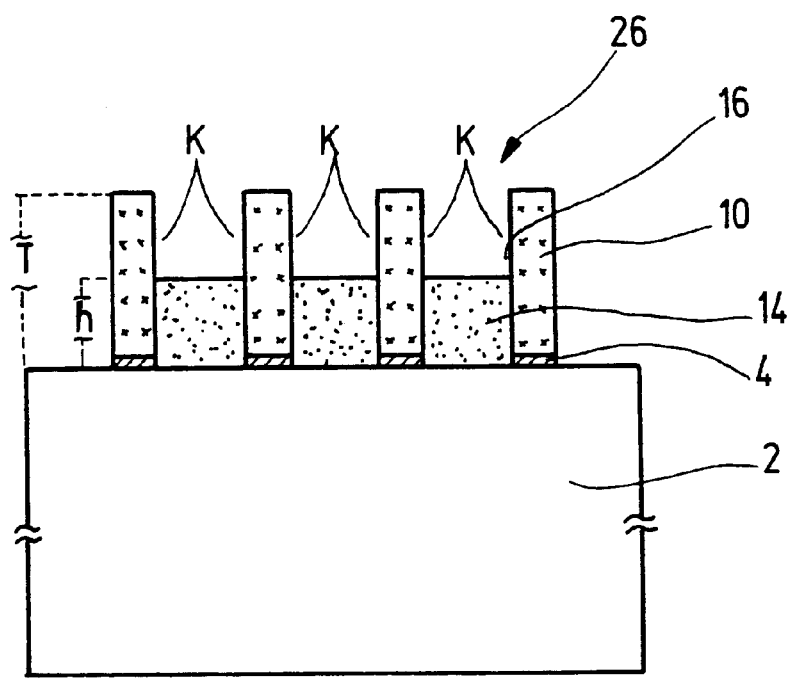
FIG. 5 schematically shows the use of inner walls of the three-dimensional electrode arrangement, depicted in longitudinal section, for wall catalysis.
Figure 6:
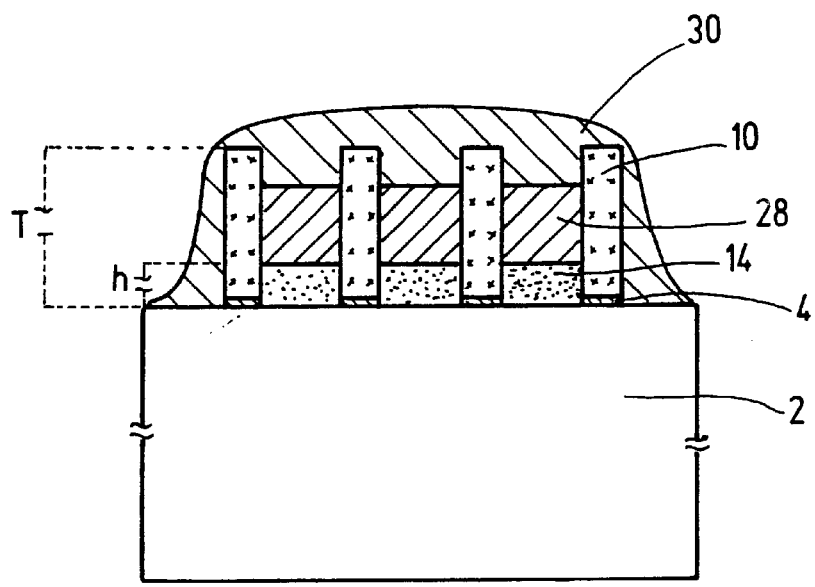
FIG. 6 schematically shows the use of the three-dimensional electrode arrangement, depicted in longitudinal section, as a retaining structure for catalyst layers and protective layers.

In step h), (FIG. h) a paste is placed into the interstices between electrodes 10 using the screen-printing method; this is then sintered at several hundred degrees, which forms layer 14 containing the gas-sensitive material. The paste is layered to a specific height h which is less than the depth T of the trenches and or the three-dimensional electrodes 10. Further layers, for example protective layers or catalytically active layers, can be applied over gas-sensitive layer 14 between electrodes 10, as depicted in FIG. 6. Especially when platinum is used as the electrode material, inner walls 16 of electrodes 10, which are not covered by gas-sensitive layer 14, can be used for catalysis K, as depicted in FIG. 5.

FIGS. 2–4 and 7–9 schematically shown, in plan view, example electrode arrangements which effectively utilize the entire surface of the sensor. Although the depiction is two-dimensional, the electrode arrangements depicted have a three-dimensional form. Functionally identical structures are labeled with identical reference numbers.

Figure 2:
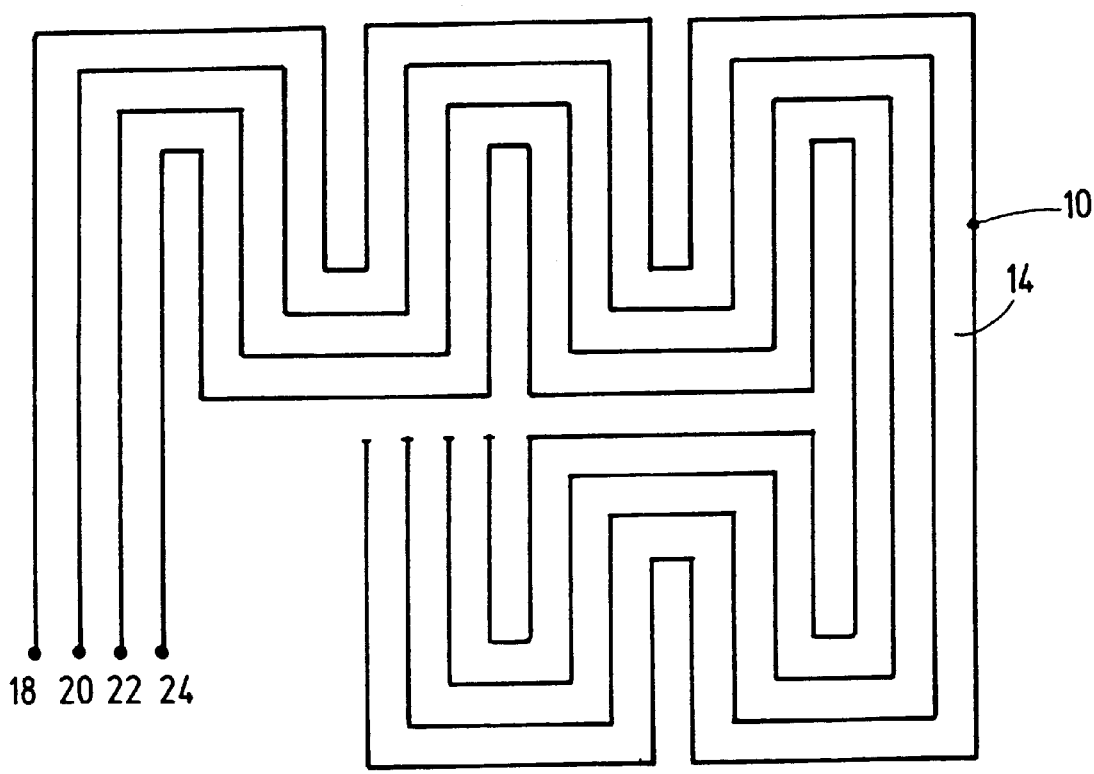
FIG. 2 schematically shows, in a two-dimensional depiction, a meander-shaped, three-dimensional, four-pole electrode arrangement.

FIG. 2 depicts a three-dimensional electrode arrangement with four-pole geometry according to an example embodiment of the present invention. Four individual electrodes 18, 20, 22, and 24, which correspondingly allow four-pole measurements, are depicted. Four-pole measurement offers the advantage over two-pole measurement that any contact resistances which occur are sensed instrumentally and can thus be eliminated. It is also evident from FIG. 2 that electrodes 18, 20, 22, and 24 are coiled for effective surface area utilization; the condition that the same electrodes must always face one another must be observed. Otherwise leakage currents would occur, decreasing the sensor sensitivity. FIG. 2 depicts an electrode arrangement with a meander structure, in which the four electrodes 18, 20, 22, and 24 are uninterrupted. In addition to this rectilinearly arranged coiling, any other electrode geometries, with curved or zig-zagging layouts, can also be provided in accordance with the present invention.

Figure 3:
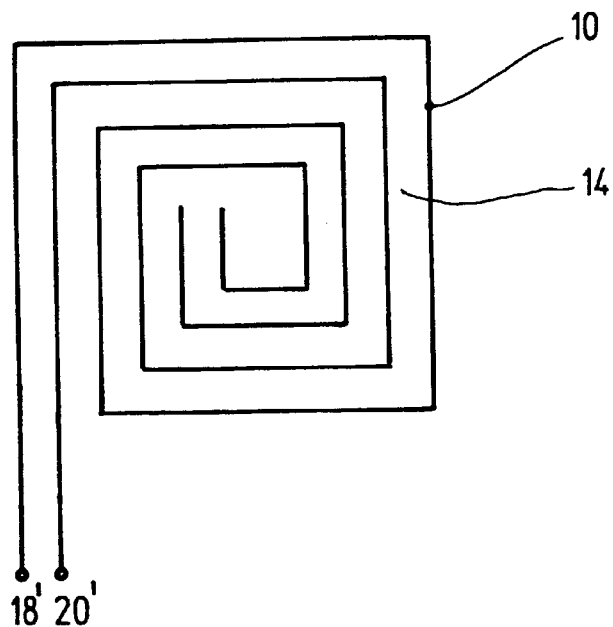
FIG. 3 schematically shows, in a two-dimensional depiction, a rectangular, three-dimensional, two-pole electrode arrangement.

FIG. 3 depicts a three-dimensional electrode arrangement of electrodes 18' and 20' in a two-pole geometry according to an example embodiment of the present invention. The electrodes are arranged in meander fashion, the electrodes running in a rectilinear internally coiled shape.

Figure 4:
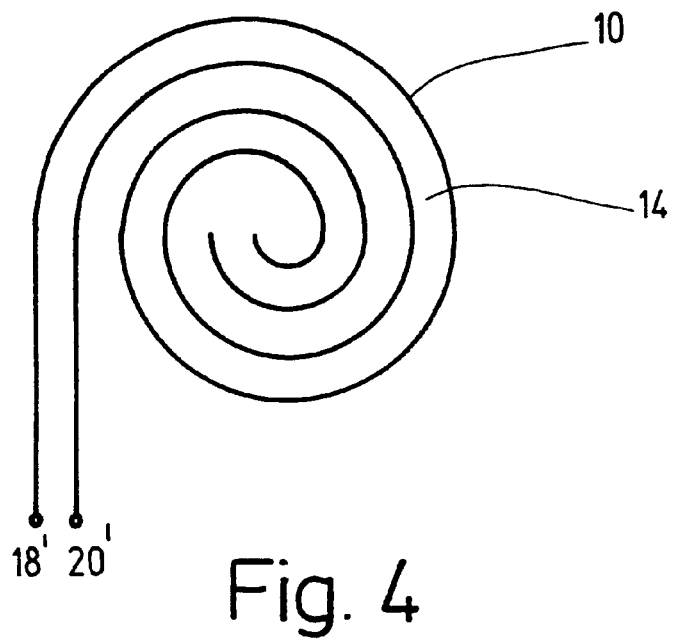
FIG. 4 schematically shows, in a two-dimensional depiction, a spiral-shaped, three-dimensional, two-pole electrode arrangement.

FIG. 4 depicts a three-dimensional arrangement of electrodes 18' and 20' in two-pole geometry with a spiral electrode layout according to an example embodiment of the present invention. As in the previous figures, the purpose of the electrode structure is to achieve good surface area utilization on the support plate. The electrode layout can of course be adapted to the lateral heat distribution on the substrate, so that the sensor region can be laid exactly on an isothermal surface.

FIG. 5 illustrates that fill height h of gas-sensitive layer 14 is less than depth T of trenches 26 enclosed by electrodes 10. Inner walls 16 of electrodes 10, which are not covered by gas-sensitive material 14, are preferably catalytically active, especially when platinum is used as the electrode material. The gas to be detected is catalytically converted on the inner walls so that it can be detected by gas-sensitive layer 14 located therebeneath.

FIG. 6 illustrates a further embodiment of the present invention, in which two further layers have been applied over the gas-sensitive layer. Gas-sensitive layer 14, filled up to a height h, is covered by a layer 28 which catalytically converts the gas that is to be detected, so that it can be sensed in layer 14. Arranged above catalytically active layer 28 is a protective layer or cover layer 30, which protects the underlying layers 28 and 14 from external influences such as moisture and dirt. The three-dimensional electrode structure thus serves here as a retaining structure for catalytically active layer 28 and cover layer 30.

Figure 7:
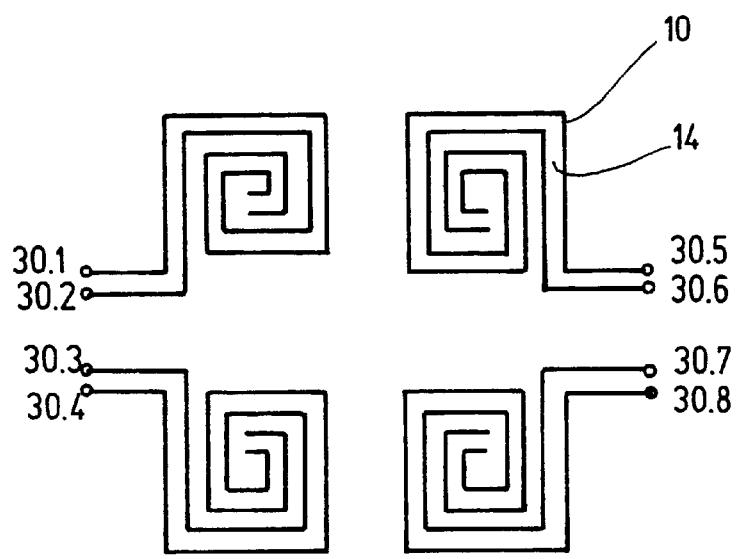
FIG. 7 shows a sensor array in a 2×2 arrangement.

FIG. 7 shows the combination of three-dimensional miniaturized electrode arrangements into a 2×2 region. The individual electrodes are labeled 30.1 through 30.8.

Figure 8:
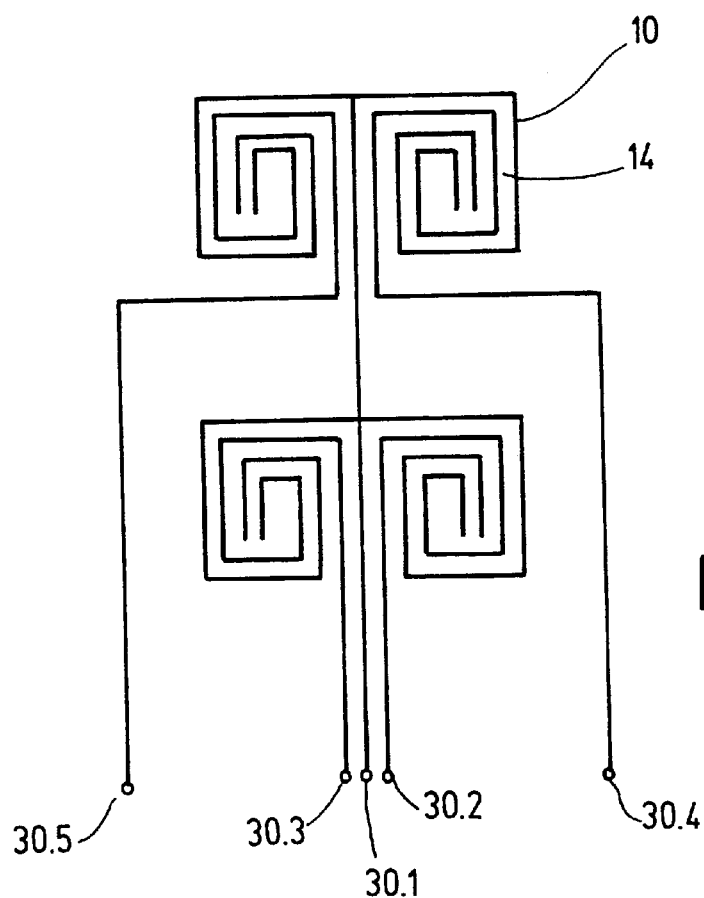
FIG. 8 shows a sensor array in a cloverleaf arrangement.

FIG. 8 shows the grouping of one three-dimensional electrode structure into a four-fold structure with a central tap which is embodied in a coiled arrangement. The four individual sensors can thereby be spatially resolved, i.e. operated so that, for example, influences of a gas flow can be compensated for. Other electrode arrangements in a cloverleaf structure are of course also possible in any desired geometry, for example as round and elliptical coils.

Figure 9:
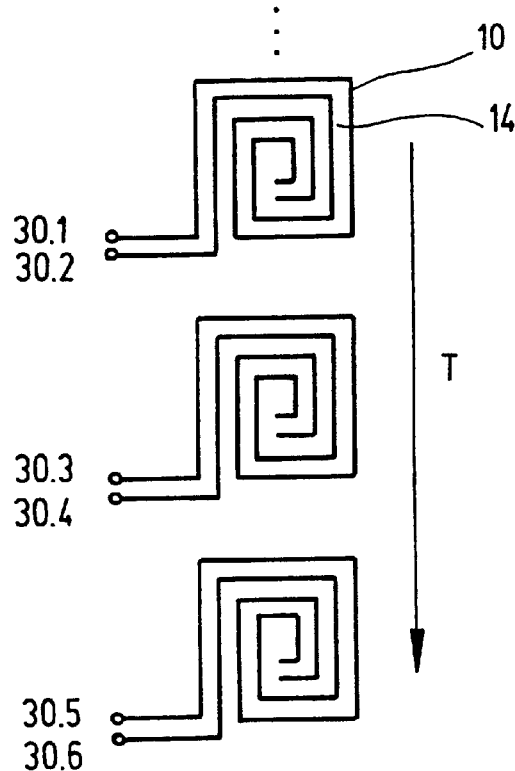
FIG. 9 shows a sensor array for temperature-dependent measurements.

FIG. 9 illustrates the arrangement of individual sensors along a defined temperature gradient T. This embodiment makes possible temperature-dependent measurements by individual interrogation of the sensors. The temperature gradient T is defined by the heater on the rear side of support plate 2.

Configuration of the sensor arrays depicted in FIGS. 7 through 9 is made possible in particular by the miniaturization made possible by three-dimensional patterning. Arrangement in arrays can make possible spatially resolved measurements, and the detection of different gases by the use of multiple gas-sensitive substances.

What is claimed is:

1. A sensing element, comprising:

a support plate;

at least one three-dimensional arrangement of electrodes applied on the support plate, the arrangement of electrodes forming trenches of a depth of between 10 $\mu$m and 100 $\mu$m;

a gas-sensitive layer arranged to a predetermined height only in the trenches, the arrangement of electrodes measuring changes in at least one of potential, capacitance and conductivity in the gas sensitive layer, the predetermined height of the gas-sensitive layer being less than the depth of the trenches; and a catalytically active layer covering the gas sensitive layer.

2. The sensing element according to claim 1, further comprising:

a protective layer that is arranged in the trenches above one of the gas-sensitive layer and the catalytically active layer.

3. The sensing element according to claim 1, wherein the electrodes of the at least one three-dimensional arrangement of electrodes are arranged in the form of an interdigitated structure.

4. The sensing element according to claim 1, wherein the at least one three-dimensional arrangement of electrodes is formed from four individual electrodes, which allow a four-pole measurement.

5. The sensing element according to claim 1, wherein the support plate includes one of ceramic material, glass, aluminum oxide and a silicon/silicon dioxide mixture.

6. The sensing element according to claim 1, wherein the electrodes of the at least one arrangement of electrodes includes one of platinum, gold, silver, copper and nickel.

7. A sensing element, comprising:

a support plate;

at least two three-dimensional arrangements of electrodes applied on the support plate, the arrangements of electrodes forming trenches of a depth of between 10 $\mu$m and 100 $\mu$m;

a gas-sensitive layer arranged to a predetermined height only in the trenches, the arrangements of electrodes measuring changes in at least one of potential, capacitance and conductivity in the gas sensitive layer, the predetermined height of the gas-sensitive layer being less than the depth of the trenches; and a catalytically active layer covering the gas sensitive layer.

8. An electrochemical sensor for determining a gas concentration, comprising:

at least one of a sensing element and sensor array, the at least one sensing element and sensor array, including a support plate, at least one three-dimensional arrangement of electrodes applied on the support plate, the arrangement of electrodes forming trenches of a depth of between 10 $\mu$m and 100 $\mu$m, a gas-sensitive layer arranged to a predetermined height only in the trenches, the arrangement of electrodes measuring changes in at least one of potential, capacitance and conductivity in the gas sensitive layer, the predetermined height of the gas-sensitive layer being less than the depth of the trenches, and a catalytically active layer covering the gas sensitive layer.

9. A method for manufacturing a sensing element having a three-dimensional electrode arrangement, comprising the steps of: depositing an electroplating starter layer onto a support plate; applying a photoresist at a thickness of between 10 $\mu$m to 100 $\mu$m onto the electroplating starter layer; patterning the photoresist to form resist trenches; filling the resist trenches by electroplating up to a defined height; removing the photoresist to form electrode trenches; etching away the electroplating starter layer from within the electrode trenches; placing a gas sensitive material into the electrode trenches up to a predetermined height that is less than the depth of the electrode trenches; and applying a catalytically active material onto the gas sensitive material in the electrode trenches.

* * * * *